(12) United States Patent
Kangas

(10) Patent No.: US 7,544,381 B2
(45) Date of Patent: Jun. 9, 2009

(54) LUBRICIOUS COATINGS FOR MEDICAL DEVICE

(75) Inventor: Steve Kangas, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1036 days.

(21) Appl. No.: 10/658,729

(22) Filed: Sep. 9, 2003

(65) Prior Publication Data

US 2005/0055044 A1 Mar. 10, 2005

(51) Int. Cl.
*B05D 3/06* (2006.01)
*A61L 27/50* (2006.01)
*C03C 25/24* (2006.01)

(52) U.S. Cl. .................. 427/2.1; 427/558; 522/32; 522/149; 522/96; 522/109

(58) Field of Classification Search ......... 427/2.1–2.31, 427/558; 522/32, 96, 149
See application file for complete search history.

(56) References Cited

U.S. PATENT DOCUMENTS

| | | | | |
|---|---|---|---|---|
| 4,272,620 A | * | 6/1981 | Ichimura | 525/61 |
| 4,564,580 A | | 1/1986 | Ichimura et al. | 430/281 |
| 4,777,114 A | | 10/1988 | Ichimura et al. | 430/270 |
| 4,891,300 A | | 1/1990 | Ichimura et al. | 430/283 |
| 5,021,505 A | | 6/1991 | Ichimura et al. | 525/59 |
| 5,206,113 A | | 4/1993 | Mueller-Hess et al. | 430/270 |
| 5,576,072 A | | 11/1996 | Hostettler et al. | 427/532 |
| 5,662,960 A | | 9/1997 | Hostettler et al. | 427/2.3 |
| 5,693,034 A | * | 12/1997 | Buscemi et al. | 604/265 |
| 5,849,368 A | | 12/1998 | Hostettler et al. | 427/536 |
| 5,919,570 A | | 7/1999 | Hostettler et al. | 428/424.8 |
| 6,017,577 A | | 1/2000 | Hostettler et al. | 427/2.12 |
| 6,030,656 A | | 2/2000 | Hostettler et al. | 427/2.3 |
| 6,040,058 A | | 3/2000 | Hostettler et al. | 428/457 |
| 6,080,488 A | | 6/2000 | Hostettler et al. | 428/423.3 |
| 6,120,904 A | | 9/2000 | Hostettler et al. | 428/423.3 |
| 6,176,849 B1 | | 1/2001 | Yang et al. | 604/265 |
| 6,265,016 B1 | | 7/2001 | Hostettler et al. | 427/2.11 |
| 6,331,578 B1 | | 12/2001 | Turner et al. | 523/105 |
| 6,458,867 B1 | | 10/2002 | Wang et al. | 523/105 |
| 6,558,798 B2 | | 5/2003 | Zhong et al. | 428/420 |
| 6,589,215 B2 | | 7/2003 | Yang et al. | 604/265 |
| 6,610,035 B2 | | 8/2003 | Yang et al. | 604/265 |
| 2001/0027299 A1 | | 10/2001 | Yang et al. | 604/265 |
| 2002/0022194 A1 | | 2/2002 | Morigaki | 430/286.1 |

FOREIGN PATENT DOCUMENTS

EP 0373537 6/1990
EP 0373862 6/1990

OTHER PUBLICATIONS

Pourciel, Development of Photo-Polymerisable Polyvinyl Alcohol for Biotechnological Applications, Apr. 28, 2003, pp. 330-336.

* cited by examiner

*Primary Examiner*—William Phillip Fletcher, III
*Assistant Examiner*—Cachet I Sellman
(74) *Attorney, Agent, or Firm*—Vidas, Arrett & Steinkraus, P.A.

(57) ABSTRACT

An ultraviolet curable lubricious coating including at least one lubricious polymer and at least one oxygen-insensitive crosslinkable polymer, methods of making and using the same, and articles coated therewith.

11 Claims, 1 Drawing Sheet

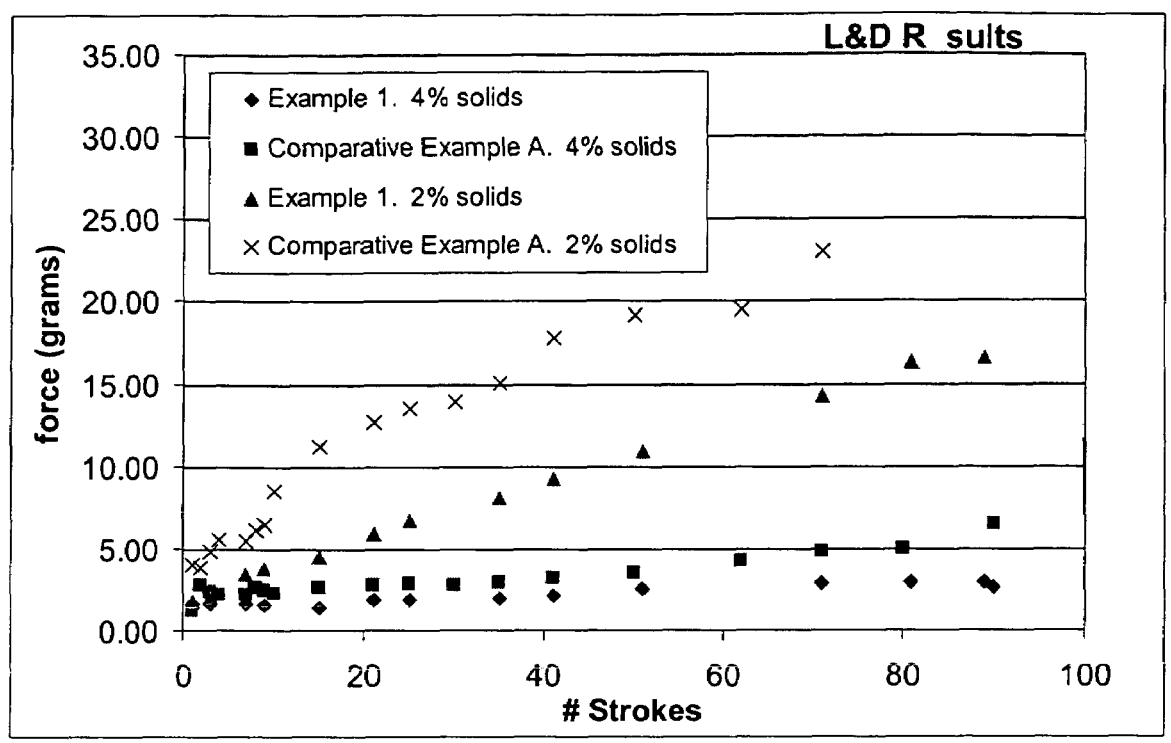

LUBRICIOUS COATINGS FOR MEDICAL DEVICE

FIELD OF THE INVENTION

This invention relates generally to the field of synthetic polymeric coating compositions for polymeric and metal substrates, to methods of making and using the same, and to articles coated therewith.

BACKGROUND OF THE INVENTION

Water soluble, biocompatible compounds that impart lubricity to the surface of otherwise non-lubricious materials are desirable for use on medical devices which are inserted or implanted into the body. Such medical devices may include catheters that are utilized to deliver a stent, stent-graft, graft or vena cava filter, balloon catheters, other expandable medical devices and so forth. The industry has turned to hydrophilic lubricious coatings in order to overcome problems with commonly used hydrophobic coatings such as silicone, glycerin or olive oil.

Hydrophobic coatings have been known to bead up and run off when exposed to an aqueous environment, lose initial lubricity rapidly, and lack abrasion resistance. Residual amounts of silicone have also been known to cause tissue reaction and irritation in patients. The loss of lubricity can lead to discomfort during insertion into a patient, and damage to blood vessels and tissues due to frictional forces during insertion or removal of the device.

Hydrophilic coatings can be difficult to retain on the surface of a medical device when exposed to an aqueous environment such as that of bodily fluids. One particular class of hydrophilic coatings which has become popular for use are "hydrogels" which swell in an aqueous environment, and are capable of manifesting lubricity while in a "wet" or hydrated state. When hydrated, these substances have low frictional forces in humoral fluids including saliva, digestive fluids and blood, as well as in saline solution and water. Such substances include polyethylene oxides, optionally linked to the substrate surface by urethane or ureido linkages or interpolymerized with poly(meth)acrylate polymers or copolymers; copolymers of maleic anhydride; (meth)acryl amide polymers and copolymers; (meth)acrylic acid copolymers; polyurethanes; poly(vinyl pyrrolidone) and blends or interpolymers with polyurethanes; polysaccharides; and mixtures thereof.

Hydrogels alone, however, may still migrate from surfaces to which they are applied when exposed to an aqueous environment. One way in which to obtain improved surface retention has been through the use of polymeric networks in which one material is crosslinkable, or through the use of interpenetrating networks in which more than one material is crosslinkable.

The crosslinkable materials are typically cured through the addition of ultraviolet (UV) radiation. UV curable systems typically function by one of two mechanisms including a free radical mechanism or a cationic mechanism. One example of a class of materials which cure via a free radical mechanism are the acrylate functional crosslinkers. These acrylates are sensitive to oxygen in that they can form stable radicals in its presence, and thus require an inert gas purge.

Cationic cure mechanisms typically involve the use of a sulfonium or iodonium salt which decomposes when exposed to actinic UV radiation forming strong acids. This type of crosslinkable material is sensitive to the presence of a basic species and to humidity.

There remains a need in the art for an improved crosslinkable material useful in forming lubricious coatings which is not sensitive to the presence of oxygen or moisture.

SUMMARY OF THE INVENTION

In its broadest sense, the present invention relates to a lubricious coating wherein at least one component is an oxygen insensitive crosslinkable material, and at least one second component is present to provide lubricity. The lubricious coating may be employed on the surface of medical devices or components thereof.

The second component may be any lubricious polymeric material including lubricious hydrophilic polymers, lubricious hydrophobic polymers or a mixture thereof. Crosslinkable materials may also be employed.

In one aspect, the crosslinkable material is employed to form a polymeric network with a lubricious uncrosslinked hydrogel.

In another aspect, the oxygen insensitive crosslinkable component may be employed in combination with at least one second crosslinkable component, the result being a "semi-interpenetrating polymer network".

In one embodiment, the crosslinkable polymer is a polyvinyl alcohol modified with styrylpyridinium groups having the following general chemical structure:

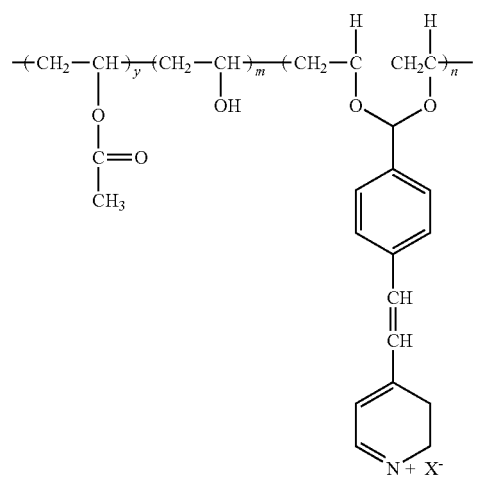

wherein y, m and n are positive numbers and X is an anion.

One advantage to using the styrylpyridinium modified PVA is that the styrylpyridinium group itself is a chromophore or light-absorbing group that initiates crosslinking, and therefore requires no photoinitiator, unlike conventional UV curable materials.

In one embodiment, the styrylpyridinium modified polyvinyl alcohol (PVA) is employed to form a polymer network with a polyethylene oxide hydrogel.

In another embodiment, the styrylpyridinium modified PVA is employed to form a polymer network with a polyurethane or a blend of polyurethanes.

The lubricious coatings may be employed on any polymeric or metallic surface to provide lubricity to such surface. The lubricious coatings find particular utility on medical devices and components thereof such as catheter shafts, guidewires, guidewire lumens, dilatation balloons, and so forth. The lubricious coatings may be employed on both inner and outer surfaces of such medical devices and components thereof.

The surface of the medical device may first be plasma treated such as with helium or argon, for example, to improve the adherence of the coating to the substrate.

The present invention further relates to a process for applying the lubricious coatings to the medical devices or components thereof. Such method includes the steps of applying the coating to the device or component thereof, and polymerizing the crosslinkable material(s) on the surface of the device by administering UV radiation to the coated surface of the device. Application of the coating may be accomplished out of solvent by spraying, brushing, painting, or so forth. Useful solvents include, but are not limited to, water, lower alcohols such as isopropanol, methanol and so forth. Extrusion, coextrusion, and other application techniques may also be employed. Such techniques do not require the use of solvents.

If the lubricious polymer is also a crosslinkable material, a photoinitiator may also be advantageously added to the coating mixture if the cure is by the addition of radiation such as ultraviolet radiation.

In another aspect, the present invention includes a drug delivery system wherein the coating is secured to a device insertable into a living body, wherein the coating includes the oxygen-insensitive crosslinkable material, an uncrosslinked hydrogel, and a therapeutic drug. The therapeutic drug may be entrapped in the coating or can be leachable from the coating upon hydration of the coating.

BRIEF DESCRIPTION OF THE DRAWINGS

FIG. 1 is a graph showing the force required to cycle a latex pad across a hydrated catheter according to the present invention as compared to the force required for a prior art catheter.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

The lubricious coatings include at least one oxygen-insensitive crosslinkable polymer and at least one lubricious polymer.

It has been found advantageous to employ an oxygen-insensitive crosslinkable polymer having styrylpyridinium groups. The styrylpyridinium groups may be added to the backbone of a polymer chain by a condensation reaction, for example. In one embodiment, the styrylpyridinium groups are added via a condensation reaction to the backbone of a polymer chain having adjacent hydroxyl groups, thus forming an acetal linkage.

A more specific example of a useful oxygen-insensitive crosslinkable polymer is one in which the styrylpyridinium groups were added to a polyvinyl alcohol (PVA) by a condensation reaction which formed an acetal linkage. The compound has the following general structure:

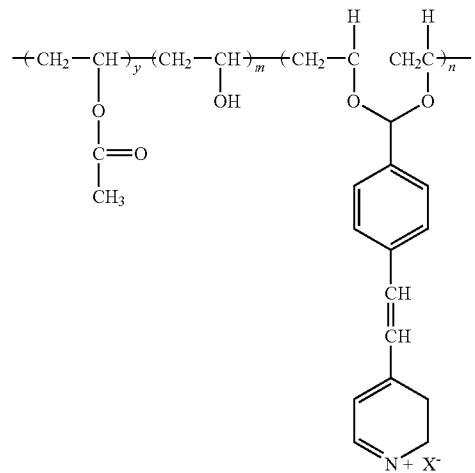

wherein y, m and n are positive numbers, and X is an anion.

X may be sulfate ($SO_3^-$), carbonate ($CO_2^-$), a halide ion such as $Cl^-$, $Br^-$, hydrogensulfate ($HSO_3^-$), an alkylsulfate such as $CH_3SO_3^-$, phosphate ion, p-toluene sulfonate ion, naphthalene sulfonate, methyl sulfate ion, ethyl sulfate ion, phosphite, tetrafluoroborate, hexafluorophosphate, chloride-zinc chloride, trifluoroacetate, oxalate, alkylsulfonate having 1 to 8 carbon atom, sulfonates such as trifluoromethane sulfonate, arylsulfonate having 6 to 24 carbon atoms and 2-hydroxy-4-methoxybenzophenone-5-sulfonate, and so forth.

The styrylpyridinium functional group cures via a cycloaddition reaction and the reaction therefore proceeds by neither a conventional free radical process nor a cationic process, although it is believed to be radical in nature. Furthermore, the styrylpyridinium group itself is a chromophore or light-absorbing group that initiates crosslinking, and therefore requires no photoinitiator, unlike conventional UV curable materials. Peak absorption occurs at about 360 nm, absorption which is ideally suited for Hg vapor lamps which are often used in industrial settings to induce crosslinking.

Polyvinyl alcohol substituted with styrylpyridinium groups is water soluble and requires no additional solvent, an additional benefit when employing the compound in a lubricious coating.

Other photosensitive groups which may be employed in the oxygen-insensitive crosslinkable polymers of the present invention include, for example, styrylquinolinium groups and styrylbenzothiazolium groups. PVA polymers modified with such groups are described, for example, in U.S. Pat. No. 5,021,505 which is incorporated by reference herein in its entirety.

Other polymeric materials to which the styrylpyridinium groups may be added include, for example, polyvinylpyrrolidones or polyacrylic acids, for example.

Upon addition of UV energy to the styrylpyridinium modified PVA, a crosslinking reaction takes place between the styrylpyridinium groups and is believed to proceed according to the following mechanism:

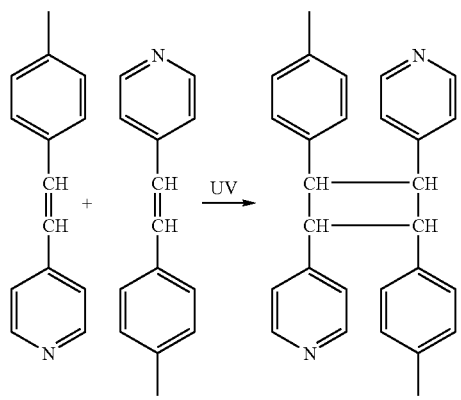

This reaction proceeds via a 2+2 cycloaddition rather than by a conventional free radical or cationic mechanism. Thus, the reaction is not sensitive to oxygen as is typical with free radical mechanisms as with the acrylates for example, nor is it sensitive to bases or moisture as is typical with a cationic mechanism. Styrylpyridinium groups are known to orient as shown during film formation such as during coating/drying processes. Because these groups orient in such a manner, one styrylpyridinium group does not need to diffuse through the coating medium to find another styrylpyridinium group to react with. Therefore, these groups are ready for reaction even prior to addition of UV energy. The cure rate is rapid and can take as little as 30 seconds or less and appears to be insensitive to temperature, curing rapidly at temperatures as low as −80° C. The rapid cure rate is beneficial over commonly employed free radical polymers because they are diffusion controlled and cure rates tend to be slower.

These crosslinked structures are believed to trap other, more mobile lubricious polymeric materials within the crosslinked structure, thus immobilizing the lubricious material such that it does not migrate as readily from the surface to which the lubricious coating is applied.

The lubricious polymeric material may be hydrophobic, hydrophilic or a mixture thereof, and may also itself be a crosslinkable material. With noncrosslinkable hydrophobic or hydrophilic materials, the oxygen-insensitive crosslinkable compound may form polymeric networks such as those described in commonly assigned U.S. Pat. No. 5,693,034 which is incorporated by reference herein in its entirety. In the latter case wherein the lubricious polymeric material is also crosslinkable, an interpenetrating network or IPN may be formed with the oxygen-insensitive crosslinkable polymer.

Examples of useful hydrophilic polymers include, but are not limited to, poly(acrylic acid), poly(methacrylic acid), polyurethanes, polyethylene oxide (PEO), poly(N-isopolyacrylamide), or polymers of hydroxyl-substituted lower alkyl acrylates, methacrylates, acrylamide, methacrylamide, lower allylacrylamides and methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl4,4'-dialkyloxazolin-5-one, 2- and 4-inylpruidine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Such polymers are known to swell in the presence of water and become slippery, and are often referred to in the industry as "hydrogels." These polymers thus typically exhibit greater lubricity when wet. Lubricious hydrogels of this type are described in commonly assigned U.S. Pat. No. 5,693,034 incorporated by reference herein in its entirety.

In one embodiment, polyethylene oxide is employed in combination with the oxygen-insensitive crosslinkable material.

In another embodiment, a polyurethane or a blend of polyurethanes is employed in combination with the oxygen-insensitive crosslinkable material. Examples of polyurethanes which may be employed include, but are not limited to, TECOGEL® 500, TECOGEL® 2000, both of which are available from Thermedics, Inc. TECOGEL® polyurethanes are aliphatic polyether polyurethanes which can absorb anywhere from about 5 times (TG-500) to about 20 times (TG-2000) their weight in water. Used in combination with a crosslinkable material according to the present invention, results in a semi-interpenetrating polymer network (semi-IPN). The crosslinkable material suitably crosslinks with itself, but not with the polyurethane(s).

In yet another embodiment, the polyurethanes of the type described above, are blended with polyurethanes which do not absorb as much water, and thus do not swell as much. Polyurethanes exhibiting water absorption anywhere from 0% up to about 2000% as described above, are available while the TECOGEL® polyurethanes are in the range of 500% to 2000% based on their own weight. Using such blending, the amount of lubricity, or how much frictional forces are reduced, can be controlled.

Lubricious hydrophobic materials may also be employed in the present invention. The use of hydrophobic lubricious materials may require that some compatibility exist between the lubricious material and the oxygen-insensitive crosslinkable polymer in order to achieve a satisfactory amount of mixing. Examples of useful hydrophobic polymers include, but are not limited to, silicones, glycerine or olive oil, for example. Lower molecular weight hydrophobic materials may be more easily entrapped within the crosslinked structure of the oxygen-insensitive crosslinkable polymer.

In another aspect, the lubricious polymer may also be crosslinkable. A combination of crosslinkable polymers can advantageously form what is known in the art as a interpenetrating network or IPN if a second material which itself is crosslinkable is employed. IPNs are advantageously employed to obtain satisfactory intermingling of two otherwise different materials such as one which is hydrophobic, and one which is hydrophilic. It is also believed that such structures can be employed to obtain better retention on polymeric and metallic surfaces possibly through covalent bonding.

In the latter case, if a second crosslinkable material is also employed, a photoinitiator may be optionally added if the curing mechanism of the secondary crosslinkable material is achieved through the addition of UV energy. Unlike many UV curable systems, the styrylpyridinium modified polymers of the present invention require no additional photoinitiator because styrylpyridinium groups are themselves chromophores which absorb in the UV range.

Other materials not described herein could advantageously be employed according to the present invention. The above lists are not exhaustive and are intended for illustrative purposes only. There are an endless variety of polymeric materials which may be incorporated into the polymer network or IPN according to the present invention.

Other materials such as antioxidants, fluorescing agents, plasticizers, UV stabilizers, and so forth may also be employed in the mixture. Such materials are known to those of ordinary skill in the art.

The lubricious coatings according to the present invention find utility on a variety of surfaces including polymeric, metallic, wood and so forth. These coatings are particularly useful on medical devices and their components including, for example, catheter shafts, guidewires, dilatation balloons, and so forth.

Some surfaces may first require a primer treatment prior to application of the lubricious coating. For example, polyolefin surfaces such as polyethylene or polypropylene may require a glow discharge plasma treatment. Other polymeric substrates, such as polyimides containing diaromatic ketones and polyethylene terephthalate, have also been found to be suitable substrates even when not plasma treated. Polyurethanes and nylons may be primed with a vinyl functional isocyanate. Metals, such as stainless steel and gold, may be first treated with a primer such as a vinyl or acrylate functional silane for best adhesion. One of ordinary skill in the art is aware of such surface treatments.

The coating find utility on both inner and outer surfaces. The lubricious coatings may, for example, facilitate delivery of a medical device through a patient's vasculature. Application of the lubricious coating to the inner surface of an inner lumen in a catheter shaft may reduce wire movement friction during the use of a guidewire, for example.

There are numerous other applications for such lubricious hydrogels as are known to those of ordinary skill in the art.

The coatings may be applied to both inner and outer surfaces by dipping, spraying, brushing, coextruding, and so forth.

The coatings may be applied to the desired surface by first mixing the lubricious polymer and the oxygen-insensitive crosslinkable material in a solvent or cosolvent mixture. Useful solvents include, for example, lower alcohols such as isopropyl alcohol, water, and so forth. The solvent may be selected based on the solubility of the crosslinkable material and the lubricious polymer. One of ordinary skill in the art is knowledgeable of such solvent selection.

Once the desired surface has been coated, the crosslinkable material may be cured by application of UV light for a short period of time. The UV light triggers the polymerization and crosslinking of the compound. Preferably, the mixture is cured using a high intensity ultraviolet lamp. The precise amount of time needed to cure the surface is dependent on the source of energy, the relative amounts of constituents in the composition, the thickness of the coating desired, and other factors. An initial cure is typically quite rapid, however, and can take as little as 30 seconds or less. However, it is possible that some curing may continue after the UV light has been removed.

Using the oxygen-insensitive crosslinkable polymer offers many advantages over currently other conventionally used crosslinkable polymers. First, as noted above, no purge with an inert gas is required because it is insensitive to the presence of oxygen. A second advantage is that no photoinitiator is required to crosslink the polymer.

Third, when the oxygen-insensitive crosslinkable material is employed in combination with a noncrosslinkable hydrogel, the coating may be highly lubricious when wet. In the dry state, however, the coating is virtually indistinguishable from the substrate. This offers an advantage over some lubricious coatings that remain tacky even when in a dry state.

Fourth, the lubricious coating of the present invention can be applied to a variety of different substrates with strong adherence due to the crosslinking reaction. Thus, the polymer network or IPN, depending on the lubricious polymer selected, provides a lubricious, as well as an adherent and durable coating. Vigorous rubbing and long-term hydration do not reduce the coating's lubricity, demonstrating the strong adhesion of the coating.

Fifth, as mentioned previously, the oxygen-insensitive crosslinkable material according to the present invention can be employed in combination with a noncrosslinkable material such as a noncrosslinkable hydrogel, for example polyethylene oxide or polyvinylpyrrolidone, to form a polymer network in which the hydrogel is virtually entrapped within the system. Entrapment prevents material from leaving the coating and entering the body. This feature can be employed to entrap various polymers within the crosslinked structure including hydrophobic materials as well as hydrophilic materials.

Sixth, the polymer network of the present invention is useful as a drug delivery system. By varying such parameters as the molecular weight of the lubricious polymer and the crosslink density of the oxygen-insensitive crosslinkable polymer, an additional constituent, such as a therapeutic drug, can be incorporated into the present polymer network. The drug may also be entrapped in the polymer network or IPN and leaches out of the coating when the coating is wet delivering the drug to immediately adjacent areas of the body. The advantages of incorporating a drug which is released from the coating on medical devices is apparent. Effects of thrombus formation, restenosis, infections, and even disease transmission could be minimized or eliminated through the use of the coating of this invention.

The following non-limiting examples further illustrate the present invention.

EXAMPLES

Test Methods

1. Lubricity Test Method

Lubricity was measured using a device that cycles a latex pad along the length of a catheter. The catheter was immersed in water. The latex pad was affixed to an armature to which an 80 g weight is applied. The armature was then further connected to a force gauge. The catheter was then cycled back and forth across the pad by a motor drive. Force was measured as a function of the number of cycles. The lower the force required, the greater the lubricity.

Example 1

A hydrophilic coating was prepared using LS 400 styrylpyridinium modified polyvinyl alcohol (4.1% styrylpyridinium functional groups) available from Charkit Chemical Corp.

The coating formula used was the following:

10 parts polyethylene oxide (900,000 MW)

1 part polyvinyl alcohol modified styrylpyridinium diluted with water to 2% solids and to 4% solids Outer shafts formed from PEBAX® 7033, polyether-block-amide, and having a 0.042" diameter were first plasma treated with helium (He), sponge coated with the formula shown above, air dried at room temperature, and UV cured at 360 nm for 30 seconds on each side using a Hg vapor lamp.

The coated shafts were then tested for lubricity and durability using the Lubricity and Durability Tester.

Comparative Example A

A mixture of, polyethylene oxide in a cosolvent blend of 3.75:1 isopropyl alcohol (IPA) to water was applied to a balloon formed of PEBAX® 7033 as described above. A small amount of neopentylglycol diacrylate (NPG) crosslinker was also added to the mixture at a ratio of 10:1 PEO to NPG. Azobis-isibutironitrile photoinitiator was also added in a minimal amount effective to initiate NPG polymerization. The formula was then diluted to 2% solids and to 4% solids with water. This is an industry standard.

Outer shafts formed from PEBAX® 7033, polyether-block-amide, were sponge coated with the formula shown above, air dried at room temperature, and UV cured for 30 seconds on each side. The coated shafts were then tested for lubricity and durability using the Lubricity and Durability Tester.

The results of the above testing is shown in the following table.

TABLE 1

| | Lubricity Test, Force (g) | | | |
|---|---|---|---|---|
| Strokes | Example 1 @ 2% solids | Comp A @ 2% solids | Example 1 @ 4% solids | Comp A @ 4% solids |
| 1 | 1.80 | 2.73 4.00 | 1.60 | 1.25 |
| 2 | | 3.87 | 2.80 | 2.75 |
| 3 | 2.08 | 4.80 | 1.60 | 2.40 |
| 4 | | 5.57 | 3.00 | 2.20 |
| 7 | 3.40 | 5.50 | 1.65 | 2.20 |
| 8 | | 6.13 | 2.80 | 2.60 |
| 9 | 3.76 | 6.50 | 1.55 | 2.45 |
| 10 | | 8.50 | 3.20 | 2.30 |
| 15 | 4.48 | 11.17 | 1.40 | 2.60 |
| 21 | 5.88 | 12.70 | 1.85 | 2.80 |
| 25 | 6.68 | 13.50 | 1.90 | 2.85 |
| 30 | | 13.87 | 3.60 | 2.80 |
| 35 | 8.12 | 15.03 | 2.00 | 2.95 |
| 41 | 9.24 | 17.76 | 2.10 | 3.20 |
| 50 | | 19.11 | | 3.50 |
| 51 | 10.84 | | 2.56 | |
| 62 | | 19.47 | | 4.25 |
| 71 | 14.2 | 22.94 | 2.84 | 4.80 |
| 80 | | | | 5.00 |
| 81 | 16.24 | | 2.95 | |
| 89 | 16.52 | | 2.92 | |
| 90 | 2.60 | | 2.60 | 6.45 |

FIG. 1 is a graph summarizing the data shown in Table 1. As can be seen from the graph, the frictional force required to cycle the latex pad across the catheter for is less for example 1 than for comparative example A, an industry standard. The frictional force is a measure of lubricity. The lower the force, the higher the lubricity.

The above disclosure is intended to be illustrative and not exhaustive. The description will suggest many variations and alternatives to those of ordinary skill in the art. All of these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A method of coating at least one surface of a medical device, said method comprises the steps of:
    a) applying a mixture to said at least one surface of said medical device, said mixture comprising at least one lubricious polymer and at least one polymer which is crosslinkable by an oxygen-insensitive non-cationic mechanism; and
    b) exposing said coating to ultraviolet radiation.

2. The method of claim 1 wherein said mixture is applied out of solvent.

3. The method of claim 1 wherein said mixture is applied to said surface of said medical device by spraying, dipping, painting or coextruding.

4. The method of claim 2 wherein said mixture is present at a concentration of about 1 wt-% to about 5 wt-% solids.

5. The method of claim 1 wherein said at least one polymer which is crosslinkable by an oxygen-insensitive non-cationic mechanism comprises styrylpyridinium groups.

6. The method of claim 1 wherein said at least one polymer which is crosslinkable by an oxygen-insensitive non-cationic mechanism has the following general structure:

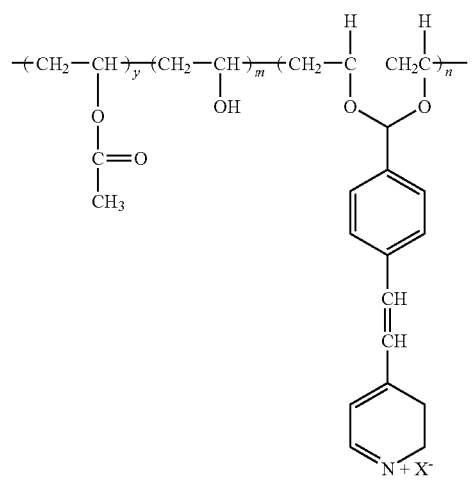

wherein y, m and n are positive numbers and X is an anion.

7. The method of claim 1 wherein said lubricious polymer comprises at least one member selected from the group consisting of comprises at least one member selected from the group consisting of but are not limited to, poly(acrylic acid), poly(methacrylic acid), polyurethanes, polyethylene oxide, poly(N-isopolyacrylamide), or polymers of hydroxyl-substituted lower alkyl acrylates, methacrylates, acrylamide, methacrylamide, lower allylacrylamides and methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl4,4-dialkyloxazolin-5 -one, 2- and 4-inylpruidine, vinylically unsaturated carboxylic acids having a total of 3 to 5 carbon atoms, amino-lower alkyl (where the term amino also includes quaternary ammonium), mono-lower alkylamino-lower alkyl and di-lower alkylamino-lower alkyl acrylates and methacrylates, allyl alcohol and mixtures thereof.

8. The method of claim 7 wherein said at least one lubricious polymer is polyethylene oxide.

9. The method of claim 7 wherein said at least one lubricious polymer is a polyurethane or a blend of polyurethanes.

10. The method of claim 9 wherein said at least one lubricious polymer is an aliphatic polyether polyurethane.

11. The method of claim 10 wherein said aliphatic polyether polyurethane is a hydrophilic aliphatic polyether polyurethane, said aliphatic polyether polyurethane is capable of absorbing about 500% to about 2000% water by weight.

* * * * *

UNITED STATES PATENT AND TRADEMARK OFFICE
CERTIFICATE OF CORRECTION

PATENT NO. : 7,544,381 B2  Page 1 of 1
APPLICATION NO. : 10/658729
DATED : June 9, 2009
INVENTOR(S) : Kangas It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 1036 days.

Delete the phrase "by 1036 days" and insert -- by 1652 days --

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,544,381 B2  
APPLICATION NO. : 10/658729  
DATED : June 9, 2009  
INVENTOR(S) : Steve Kangas Page 1 of 1

It is certified that error appears in the above-identified patent and that said Letters Patent is hereby corrected as shown below:

Column 2, Lines 30-50, delete that portion of the formula reading " 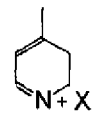 " and insert -- 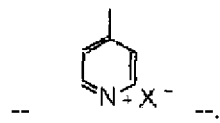 --.

Column 4, Lines 5-25, delete that portion of the formula reading " 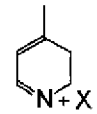 " and insert -- 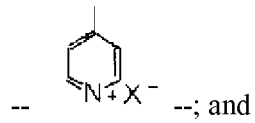 --; and Column 10, Claim 6, Lines 25-40, delete that portion of the formula reading " 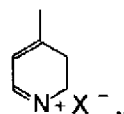 "

and insert -- 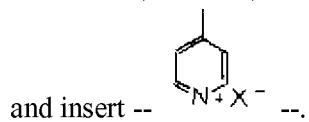 --.

Signed and Sealed this  
Third Day of January, 2012

David J. Kappos  
*Director of the United States Patent and Trademark Office*